(12) United States Patent
Kataoka et al.

(10) Patent No.: US 8,906,503 B2
(45) Date of Patent: Dec. 9, 2014

(54) FINE PARTICLES OF CRYSTALLINE POLYOL, AND METHOD OF PREPARING SAME

(75) Inventors: Kazunori Kataoka, Tokyo (JP); Kanjiro Miyata, Tokyo (JP); Nobuhiro Nishiyama, Tokyo (JP); Takehiko Ishii, Tokyo (JP); Tomoya Suma, Tokyo (JP)

(73) Assignee: University of Tokyo, Tokyo (JP)

( * ) Notice: Subject to any disclaimer, the term of this patent is extended or adjusted under 35 U.S.C. 154(b) by 173 days.

(21) Appl. No.: 13/320,314

(22) PCT Filed: May 13, 2010

(86) PCT No.: PCT/JP2010/058494
§ 371 (c)(1),
(2), (4) Date: Nov. 14, 2011

(87) PCT Pub. No.: WO2010/131777
PCT Pub. Date: Nov. 18, 2010

(65) Prior Publication Data
US 2012/0064346 A1 Mar. 15, 2012

(30) Foreign Application Priority Data

May 14, 2009 (JP) ................................. 2009-117877
May 21, 2009 (JP) ................................. 2009-123322

(51) Int. Cl.
| | | |
|---|---|---|
| B32B 5/16 | (2006.01) | |
| B32B 9/00 | (2006.01) | |
| B32B 15/02 | (2006.01) | |
| B32B 17/02 | (2006.01) | |
| B32B 19/00 | (2006.01) | |
| B32B 21/02 | (2006.01) | |
| B32B 23/02 | (2006.01) | |
| B32B 27/02 | (2006.01) | |
| C08G 69/10 | (2006.01) | |
| A61K 47/48 | (2006.01) | |
| A61K 9/51 | (2006.01) | |
| C08G 69/40 | (2006.01) | |
| C08L 77/06 | (2006.01) | |
| A61K 31/713 | (2006.01) | |
| C08J 3/12 | (2006.01) | |
| C08L 71/02 | (2006.01) | |
| C08L 77/04 | (2006.01) | |
| C12N 15/87 | (2006.01) | |
| C08G 69/48 | (2006.01) | |
| A61K 9/19 | (2006.01) | |

(52) U.S. Cl.
CPC . *A61K 9/19* (2013.01); *C08G 69/10* (2013.01); *A61K 47/48907* (2013.01); *A61K 9/5192* (2013.01); *A61K 9/5146* (2013.01); *C08G 69/40* (2013.01); *C08L 77/06* (2013.01); *A61K 31/713* (2013.01); *C08J 3/12* (2013.01); *A61K 47/48884* (2013.01); *C08L 71/02* (2013.01); *A61K 47/48238* (2013.01); *C08L 77/04* (2013.01); *C12N 15/87* (2013.01); *C08G 69/48* (2013.01); *A61K 9/5123* (2013.01); *C08J 2371/02* (2013.01); *Y10S 977/788* (2013.01); *Y10S 977/84* (2013.01)
USPC .......................... 428/402; 977/788; 977/840

(58) Field of Classification Search
USPC .................................. 428/402; 977/788, 840
See application file for complete search history.

(56) References Cited

U.S. PATENT DOCUMENTS

| | | | | | |
|---|---|---|---|---|---|
| 4,094,743 | A | * | 6/1978 | Leuba | 435/178 |
| 5,904,927 | A | * | 5/1999 | Amiji | 424/422 |
| 6,416,741 | B1 | * | 7/2002 | Sutton et al. | 424/9.52 |
| 6,537,584 | B1 | * | 3/2003 | Zentner et al. | 424/499 |
| 6,841,168 | B1 | * | 1/2005 | Worrall | 424/484 |
| 7,125,546 | B2 | * | 10/2006 | Kataoka et al. | 424/78.17 |
| 2002/0013282 | A1 | * | 1/2002 | Marshall et al. | 514/44 |
| 2003/0186271 | A1 | * | 10/2003 | Hwang et al. | 435/6 |
| 2005/0271728 | A1 | * | 12/2005 | Nomura et al. | 424/487 |
| 2006/0013885 | A1 | * | 1/2006 | Nah et al. | 424/489 |
| 2006/0111657 | A1 | * | 5/2006 | Addison et al. | 602/50 |
| 2006/0134195 | A1 | * | 6/2006 | Fu et al. | 424/464 |
| 2006/0134785 | A1 | * | 6/2006 | Fernandez et al. | 435/375 |
| 2006/0159715 | A1 | * | 7/2006 | Nagasaki et al. | 424/401 |
| 2006/0188578 | A1 | * | 8/2006 | Fernandez et al. | 424/489 |
| 2006/0241023 | A1 | * | 10/2006 | Brown et al. | 514/8 |
| 2007/0059271 | A1 | | 3/2007 | Kataoka et al. | |
| 2007/0104649 | A1 | * | 5/2007 | Fischer et al. | 424/9.6 |
| 2008/0095810 | A1 | * | 4/2008 | Fernandez et al. | 424/401 |
| 2008/0145658 | A1 | * | 6/2008 | Richard et al. | 428/402 |
| 2008/0202513 | A1 | * | 8/2008 | Birchall et al. | 128/203.15 |
| 2008/0220030 | A1 | * | 9/2008 | Fernandez et al. | 424/401 |
| 2008/0268063 | A1 | * | 10/2008 | Jon et al. | 424/491 |

(Continued)

FOREIGN PATENT DOCUMENTS

| | | |
|---|---|---|
| EP | 1 621 569 | 2/2006 |
| JP | 2004-352972 | 12/2004 |

(Continued)

OTHER PUBLICATIONS

International Search Report issued Jun. 22, 2010 in International (PCT) Application No. PCT/JP2010/058494.

(Continued)

*Primary Examiner* — Liam J Heincer
(74) *Attorney, Agent, or Firm* — Wenderoth, Lind & Ponace, L.L.P.

(57) ABSTRACT

Fine particles of crystalline polyol are provided having a cationic polymer fixed on the crystal surfaces. These fine particles can stably carry an anionically charged compound on their surfaces.

7 Claims, 8 Drawing Sheets

(56) References Cited

U.S. PATENT DOCUMENTS

| | | |
|---|---|---|
| 2008/0317864 A1* | 12/2008 | Vila Pena et al. ............. 424/499 |
| 2009/0004230 A1* | 1/2009 | Chuetz et al. ................. 424/400 |
| 2009/0004266 A1* | 1/2009 | Sung et al. .................... 424/464 |
| 2009/0014682 A1* | 1/2009 | Takahashi et al. ......... 252/62.54 |
| 2009/0155374 A1* | 6/2009 | Sung et al. .................... 424/499 |
| 2009/0169636 A1* | 7/2009 | O'Hagan et al. ............. 424/499 |
| 2010/0015177 A1* | 1/2010 | Drew ........................ 424/202.1 |
| 2010/0137512 A1* | 6/2010 | Kataoka et al. .............. 525/54.1 |
| 2010/0151436 A1* | 6/2010 | Fong et al. ..................... 435/1.1 |
| 2010/0203148 A1* | 8/2010 | He ................................ 424/493 |
| 2011/0003007 A1* | 1/2011 | Kakizawa et al. ............ 424/499 |
| 2011/0008451 A1* | 1/2011 | Saltzman et al. ............. 424/490 |
| 2011/0033547 A1* | 2/2011 | Kjems et al. .................. 424/499 |
| 2011/0142890 A1* | 6/2011 | Fernandez et al. ........... 424/401 |
| 2011/0178210 A1* | 7/2011 | Tiquet ............................. 524/27 |
| 2011/0182975 A1* | 7/2011 | Richardson et al. .......... 424/450 |
| 2011/0236412 A1* | 9/2011 | Drew ........................ 424/193.1 |
| 2012/0064346 A1* | 3/2012 | Kataoka et al. ............... 428/402 |
| 2012/0121670 A1* | 5/2012 | Lopez et al. .................. 424/401 |
| 2012/0213697 A1* | 8/2012 | Friedman et al. ............ 424/1.25 |

FOREIGN PATENT DOCUMENTS

| | | |
|---|---|---|
| JP | 2006-246766 | 9/2006 |
| JP | 2008-214324 | 9/2008 |
| JP | 2008-542342 | 11/2008 |
| WO | 2006/085664 | 8/2006 |
| WO | 2008/062909 | 5/2008 |
| WO | WO 2009006905 A1 * | 1/2009 |

OTHER PUBLICATIONS

Extended European Search Report issued Jan. 15, 2014 in corresponding European Application No. 10775027.5.

Brus et al., "Stabilization of oligonucleotide polyethylenimine complexes by freeze-drying: physiochemical and biological characterization", Journal of Controlled Release, vol. 95, No. 1, pp. 119-131, Feb. 20, 2004.

Kuo et al., "Preparation of DNA dry powder for non-viral gene delivery by spray-freeze drying: effect of protective agents (polyethyleneimine and sugars) on the stability of DNA", Journal of Pharmacy and Pharmacology, vol. 56, No. 1, pp. 27-33, Jan. 1, 2004.

* cited by examiner

FINE PARTICLES OF CRYSTALLINE POLYOL, AND METHOD OF PREPARING SAME

This application is a U.S. national stage of International Application No. PCT/JP2010/058494 filed May 13, 2010.

TECHNICAL FIELD

The present invention relates to fine particles of crystalline polyol, and relates specifically to crystalline polyol nanoparticles having a cationic polymer fixed on the surface thereof, and to a method of preparing the same.

BACKGROUND ART

It is known that nanoparticles on the scale of tens of nm (comparable to a virus) will move through blood vessels towards tumors in mammals, are unlikely to pass through the blood vessel walls and infiltrate healthy tissue and tend to accumulate easily in areas of abnormal blood vessel formation in the vicinity of tumors. As an example of nanoparticles having this effect, the inventors succeeded in effectively encapsulating anti-tumor agents and nucleic acid substances (genes (plasmid DNA) and gene-suppressing RNA chains (siRNA)) in a polymer micelle created by self-organization of a specific polymer, thereby providing a drug-encapsulating polymer micelle (see for example Patent Documents 1, 2 and 3 below).

Patent Document 1: U.S. Pat. No. 7,125,546A
Patent Document 2: EP 1621569A
Patent Document 3: WO 2006/085664

SUMMARY OF THE INVENTION

Considering the diversity of target cells and tissues to which drugs need to be delivered, however, there is still need for development of materials or carriers that can be used for more effective drug delivery.

The inventors and others discovered here that nano-sized fine particles having a narrow particle size distribution and positive surface potential could be provided by freeze-drying an aqueous solution containing a cationic polymer together with a specific compound commonly used as an excipient or adjuvant when preparing various preparations of therapeutic drugs. It was also confirmed that such fine particles could stably support anionically charged drugs for example, and could effectively deliver the supported drugs to targets such as tumor cells.

Thus, the present invention provides a method of preparing fine particles of crystalline polyol having a cationic polymer fixed on the surface thereof, which can be obtained by a process of freeze-drying an aqueous solution containing both a cationic polymer together and a crystalline polyol.

The present invention also provides fine particles of crystalline polyol, wherein a cationic polymer is fixed on the crystal surfaces of the particles.

Because they are capable of stably and effectively supporting an anionically charged drug on the surface as described above, these fine particles can be used as a carrier for various therapeutic drugs, although this is not a limitation.

BEST MODE FOR CARRYING OUT THE INVENTION

Except as otherwise specified, terms used in this Description have the same meaning with which they are commonly used in the technical field. Thus, the meaning of each term is that ordinarily used by those skilled in the art, or can be verified in standard or authoritative dictionaries used for reference.

A crystalline polyol is a water-soluble sugar, sugar alcohol, poly(ethylene glycol) or the like capable of forming a fine particle by the methods described below, and may be natural, semi-synthetic or synthetic as long as it achieves the object of the present invention. As a crystalline polyol, a water-soluble sugar, sugar alcohol or poly(ethylene glycol) that has been approved for use as a pharmaceutical excipient or adjuvant under applicable pharmaceutical law for approval of drug manufacture can be used by preference in this case.

In this description, the term crystalline or crystal means the property of assuming a solid, nonporous state at room temperature or above while exhibiting a narrow melting point, or a solid having such properties. Examples of crystalline polyols include, but are not limited to, mannitol, trehalose, xylitol, sorbitol, inositol, glucose, galactose, sucrose, mannose, fructose, ribose, xylose, dextrin and poly(ethylene glycol) having 10 to 2500 oxyethylene units (sold under the trade name Macrogol). All stereoisomers of these crystalline polyols can be used in the present invention, but it is preferable to select a stereoisomer that is used as a drug excipient or adjuvant in the technical field. Examples of such stereoisomers include, but are not limited to, isomers based on D-mannitol and D-sorbitol, as well as naturally produced isomers.

Examples of cationic polymers include polylysine, polyarginine, spermine, spermidine, chitosan, polyethyleneimine, poly(polyamine-modified aspartamide) and poly(polyamine-modified glutamide), and block copolymers containing blocks of polymer chains derived from these and blocks of polymer chains derived from poly(ethylene glycol). The molecular weights of these cationic polymers are not theoretically limited, and can be selected based on usage examples in the case of polymers that are conventionally used as carriers for nucleic acid molecules.

For purposes of use in drug delivery to target cells, poly(polyamine-modified aspartamide) and poly(polyamine-modified glutamide) are preferred out of these cationic poly- mers because of their normally low cytotoxicity. Specific examples of such cationic poly(amino acid)s include the poly (amino acid) derivatives described in Patent Document 2 or 3 above, but the polymer represented by Formula (1) below is especially preferred:

(wherein $R^1$ represents a hydroxyl group, $C_{1-12}$ optionally substituted straight or branched alkyloxy group, $C_{2-12}$ optionally substituted straight or branched alkenyloxy group, $C_{1-12}$ optionally substituted straight or branched alkynyloxy group or $C_{1-12}$ optionally substituted straight or branched alkyl-substituted imino group; $R^2$ represents a hydrogen atom, $C_{1-12}$ optionally substituted straight or branched alkyl group or $C_{1-24}$ optionally substituted straight or branched alkylcarbonyl group; $R^{3a}$ and $R^{3b}$ each independently represent a methylene group or ethylene group; $R^{4a}$ and $R^{4b}$ independently represent the same or different groups selected from the group consisting of:

and (in which p1 to p4, q1 to q6 and r1 and r2 are all independently integers from 1 to 20, n is an integer from 0 to 5,000, and y is an integer from 0 to 5,000, but when $R^{3a}$ and $R^{3b}$ are methylene groups, n is 5 or greater, and y is an integer smaller than n)).

The polymer represented by Formula (2) below is a typical example of a block copolymer containing blocks of polymer chains derived from these cationic polymers and blocks of polymer chains derived from poly(ethylene glycol):

(in which $R^2$, $R^{3a}$, $R^{3b}$, $R^{4a}$, $R^{4b}$, n and y are defined as in Formula (1) above; $L^1$ is —S—S— or a valence bond; $L^2$ is —NH—, —O—, —O(CH$_2$)$_{p1}$—NH— or -L$^{2a}$-(CH$_2$)$_{q1}$-L$^{2b}$-, with p1 and q1 each being independently an integer from 1 to 20; $L^{2a}$- is OCO, OCONH, NHCO, NHCO, NHCOO, NHCONH, CONH or COO and $L^{2b}$ is NH or O; $R^5$ is a hydrogen atom or optionally substituted $C_{1-12}$ straight or branched alkyl group; and m is an integer from 30 to 20,000).

The n and y representing the numbers of repeating units of amino acid in Formulae (1) and (2) above may each independently be 0 to 5,000, but from the standpoint of ease of synthesis, they can be 30 to 300 or preferably 60 to 150.

The block copolymer represented by Formula (2) can also be provided. In Formula (2), $R^2$, $R^{3a}$, $R^{3b}$, $R^{4a}$, $R^{4b}$, n and y are defined as in Formula (1) above.

$L^1$ is —S—S— or a valence bond, $L^2$ is —NH—, —O—, —O(CH$_2$)$_{p1}$—NH— or -L$^{2a}$-(CH$_2$)$_{q1}$-L$^{2b}$-, with p1 and q1 each being independently an integer from 1 to 20, and $L^{2a}$ is OCO, OCONH, NHCO, NHCO, NHCOO, NHCONH, CONH or COO while $L^{2b}$ is NH or O. In this definition, $L^1$ and $L^2$ must combine together to form a single linking group. For example, if $L^2$ is —NH—, $L^1$ is a valence bond rather than —S—S—. A preferred combination of -$L^1$-$L^2$- is one that forms a linking group with —S—S— as $L^1$.

$R^5$ is a hydrogen atom or an optionally substituted $C_{1-12}$ straight or branched alkyl group, examples of which include those explained for $R^1$ above. m, which represents the number of repeating units of ethylene glycol (or oxyethylene), is an integer from 30 to 20,000 or preferably 200 to 2000 or more preferably 500 to 1000. Each group and part in the formula is bound in the orientation shown.

A cationic poly(amino acid) such as those described above exhibits acid dissociation constants (pKa) at multiple levels by supporting side-chains having multiple different amine functional groups in the part containing the cationic groups, and for example under biological conditions of pH 7.4 the multiple amine functional groups are in a partially protonated state, capable of forming a polyion complex (PIC) with a nucleic acid molecule for example. It appears that when the PIC thus formed is incorporated into the endosome (pH 5.5), the cationic poly(amino acid) is further protonated under the lower pH conditions, and can move efficiently from the endosome into the protoplasm by means of a buffer effect (proton sponge effect) or endosome-selective membrane damage, allowing for drug delivery with low cytotoxicity. Consequently, such a cationic polymer exhibiting multiple-stage pKa values is preferred.

Although the content or technical scope of the present invention is not restricted by any theory, it appears that when a crystalline polyol such as those described above and a cationic polymer such as those described above are contained together in an aqueous solvent with the former in a crystallizable state, the cationic polymer is adsorbed on the surfaces of crystals derived from the crystalline polyol (surfaces which tend to be anionically charged due to deprotonation of hydroxyl groups in the polyol), and crystal growth is controlled or inhibited, resulting in fine crystals nanometers (nm) in sized with such a narrow degree of particle dispersion that they can be called monodispersed. Consequently, these fine particles have a structure comprising crystal cores derived from the crystalline polyol with the cationic polymer fixed either as a shell or a partial surface layer on the surfaces of the crystals. Moreover, it appears that when the cationic polymer is a block polymer comprising blocks of polymer chains derived from the cationic polymer and blocks of polymer chains derived from poly(ethylene glycol) as described above, some or most of the poly(ethylene glycol) chains (which have affinity for the crystalline polyol) are incorporated into the crystals of crystalline polyol, leaving the polymer chains derived from the cationic polymer arrayed on the fine crystal surfaces.

In the present invention, an aqueous solvent or solvent of an aqueous solution can be water, pure water, deionized water, or a solution comprising water and an organic solvent (ethanol, acetone, dimethylformamide, dimethylsulfoxide or the like) or buffering agent that is miscible with water.

To say that the cationic polymer is "fixed" or "supported" on the crystal surfaces of the crystalline polyol as described above means that the properties of the crystal surfaces as modified with the cationic polymer are not substantially altered by gentle agitation treatment in pure water, or in other words that for example the zeta ($\zeta$) potential contributed by the cationic polymer to the crystals or fine particle surfaces does not change substantially or significantly, and that they are capable of binding in an aqueous solvent with a specific anionically charged nucleic acid molecule (such as siRNA). The average particle diameter of these crystals or fine particles as measured in pure water is a few µm or less, or preferably 10 to 1000 nm, or more preferably 20 to 500 nm, or especially 50 to 200 nm, and the surface $\zeta$ potential is positive, or preferably +10 mV or more.

Since the surfaces of the fine particles of the present invention are cationically charged as discussed above, they can form a polyion complex with an anionically charged compound or drug in an aqueous solvent. Such an anionically charged compound may be in the form of a pure compound or a complex or other compound, or may be a protein, lipid, peptide, nucleic acid or the like without regard for the type of compound as long as it is capable of forming a polyion complex with the fine particles in an aqueous solvent, and is a drug or the like that has some significant effect on a target when delivered or bound to a specific site in an organ or part of the body. In particular, the fine particles of the present invention are strongly recommended for binding to nucleic acids and their derivatives, although this is not a limitation. As discussed above, in the fine particles of the present invention the drug is not enveloped substantially in the core part of a polymer micelle as described in Patent Documents 1 to 3 above, but is adsorbed and bound to the fine particle surfaces. Although it appears to exist substantially on the fine particle surfaces, such a drug can provide a stable aggregate or PIC under physiological conditions with the fine particles of the present invention even if the drug itself is a nucleic acid with a small molecular weight. Such a nucleic acid is defined as a poly- or oligonucleotide in which the basic units are nucleotides made up of purine or pyrimidine bases, pentose and phosphoric acid, and examples include oligo- or poly-double-stranded RNA, oligo- or poly-double-stranded DNA, oligo- or poly single-stranded DNA and oligo- or poly-single-stranded RNA. Oligo- or poly-double-stranded nucleic acids and oligo- or poly-single-stranded nucleic acids comprising a mixture of RNA and DNA in the same chain are also included. The nucleotides contained in the nucleic acid may be natural nucleotides or chemically modified non-natural nucleic acids, and they may also have amino groups, thiol groups and other substituents as well as fluorescent compounds and other molecules added thereto. The length of the nucleic acid is not particularly limited but can be 4 to 20,000 bases or preferably 10 to 10,000 bases or more preferably 10 to 55 or especially 18 to 30 bases. From the standpoint of function or effect, examples include plasmid DNA, siRNA, micro RNA, shRNA, antisense nucleic acids, decoy nucleic acids, aptamers, ribozymes and the like.

For example, any siRNA designed by known methods for a target gene or polynucleotide can form a conjugate or PIC with the fine particles of the present invention. For the chain length of the siRNA, the part forming a double strand can preferably be 15 to 50 nucleotide sequences or more preferably 18 to 30 nucleotide sequences. Known compounds in the technical field and all nucleotides having a similar action or function to these are included. Specific examples of siRNA are not particularly limited, but can be designed with reference to genes that are targets of gene therapy. Examples of such genes include, but are not limited to, PKCα (associated with non-small cell lung cancer and the like), BCL-2 (associated with malignant melanoma and the like), ICAM-1, associated with Crohn's disease), HCV (associated with hepatitis C), TNFα (associated with rheumatoid arthritis or psoriasis), adenosine receptor AI (associated with asthma), c-raf kinase (associated with ovarian cancer and the like, H-ras (associated with pancreatic cancer and the like), c-myc (associated with coronary disease), PKA Ria (associated with colon cancer), HIV (associated with AIDS), DNA methyltransferase (associated with solid tumors), VEGF receptor (associated with cancer), ribonucleotide reductase (associated with kidney cancer), CMV IE2 (associated with CMV retinitis), MMP-9 (associated with prostate cancer), TGFβ2 (associated with malignant glioma), CD49d (associated with multiple sclerosis), PTP-1B (associated with diabetes), c-myb (associated with cancer), EGFR (associated with breast cancer and the like), and mdr1, autotaxin and GLUT-1 genes (associated with cancer). Any antisense nucleic acid that is well known in the field or has the same action or function as such can also form a PIC in accordance with the present invention.

The poly(amino acid) represented by Formula (1) can be manufactured for example from a poly(amino acid ester) manufactured by polymerization of an N-carboxy anhydride derived from a known aspartate or glutamate, by using polyamines corresponding to polyamine residues of the $R^{4a}$ and $R^{4b}$ bases in aminolysis to thereby introduce polyamine residues into the side chains of the poly(amino acid) (see for example K. Miyata et al., J. Am. Chem. Soc. 2008, 130, 16287-16294, WO 2006/085664 A (Patent Document 3) and WO 2007-099660 A). The block copolymer represented by Formula (2) can be manufactured by a method of linking known poly(ethylene glycol) segments with the poly(amino acid) manufactured above (Refer to Patent Document 3).

The fine particles of the present invention can be prepared efficiently by freeze-drying an aqueous solution containing both a crystalline polyol and any cationic polymer such as the aforementioned preferred cationic poly(amino acid). Such an aqueous solution containing both can be prepared either by separately preparing aqueous solutions of the cationic polymer and crystalline polyol and then mixing the two, or by adding the cationic polymer and crystalline polyol to a single aqueous solvent, either simultaneously or in tandem.

Freeze-drying is a method of drying by reducing pressure in a frozen state to remove water and sublimable substances from a sample, and can be accomplished by ordinary freeze-drying operations or improved forms of these operations. Thus, an aqueous solution containing the aforementioned cationic polymer and crystalline polyol can be frozen with a suitable freezer, and then dried under reduced pressure in a frozen state in a degasifier equipped with a decompressor. The average particle diameter of the resulting particles can be adjusted to a certain extent by altering the freezing speed and/or the solvent concentration of the aqueous solution, but rapid freezing at an extremely low temperature such as at or below the temperature of liquid nitrogen for example, is sufficient for forming fine particles. The freeze-drying operation is performed under reduced pressure suitable for withdrawal of the aqueous solvent by suction. It is convenient to use a freeze-drying unit (DRC-1000/FDU1100 (shelf type) or FDU-2100 (manifold type): EYELA) to perform these operations, but this is not a limitation.

In the aqueous solution containing the crystalline polyol and cationic polymer, the concentrations can generally be adjusted to 0.1 to 10 w/v % or preferably 0.25 to 5 w/v % of the crystalline polyol aqueous solution and 1 to 1000 µg/mL or preferably 10 to 500 g/ml of the cationic polymer aqueous solution. An aqueous dispersed solution containing the fine particles of the present invention can be obtained by subjecting the aqueous solution thus prepared to the aforementioned freeze-drying operation, followed by rehydration.

Such an aqueous dispersed solution can be purified as is by filtration, precipitation or the like as appropriate, and an anionically charged compound or drug can then be added to the aqueous solution, agitated gently and incubated (or let sit) to thereby cause the anionically charged compound to be supported or adsorbed on the surfaces of the fine particles. The surface potential of the fine particles can then be measured as shown in the examples below for example to confirm whether supporting or adsorption has occurred. Normally, a good dispersed state can be maintained in an aqueous solution of the resulting fine particles if the surface potential of the final fine particles is maintained in a positive state.

Another possible method of preparing fine particles with an anionically charged compound supported or absorbed on the particle surfaces is to prepare an aqueous solution containing the anionically charged compound in addition to the cationic polymer and crystalline polyol, and subject this solution to the aforementioned freeze-drying operation.

SPECIFIC EMBODIMENTS OF THE INVENTION

To avoid undo complexity in explaining the present invention, the present invention is explained below using a specific crystalline polyol, cationic polymer and nucleic acid molecule together with specific operations, but the present invention is not limited to these.

MANUFACTURING EXAMPLE 1

Manufacture of poly(N-(2-aminoethyl)-aminoethylaspartamide)

Poly(β-benzyl-L-aspartate) (PBLA; degree of polymerization: approximately 100) was synthesized by ring-opening polymerization of β-benzyl L-aspartate N-carboxyanhydride (BLA-NCA) dissolved in a mixed solvent of N,N-dimethylformamide (DMF) and dichloromethane using an n-butylamine initiator. The PBLA (513 mg) was then freeze-dried with benzene and dissolved in 25 mL of N-methyl-2-pyrrolidone (NMP), diethylene triamine (DET) equivalent to 50 times the amount of benzyl ester was mixed with the same amount of NMP, and the PBLA solution was added to the DET solution in argon at 0° C., and reacted for 1 hour. This was added to cooled 5 N HCl aqueous solution, purified by dialysis at 4° C. with 0.01 N HCl followed by pure water, and collected by freeze-drying. The target poly(N-(2-aminoethyl)-aminoethylaspartamide) (abbreviated hereunder as PAsp(DET)) was thus obtained as a white powder.

MANUFACTURING EXAMPLE 2

Manufacture of poly(ethylene glycol)-block-PAsp(DET) copolymer

Poly(ethylene glycol) with one methoxy terminal, one aminopropyl terminal and an average molecular weight of 12,000 was dissolved in dichloromethane, and BLA-NCA dissolved in a mix solvent of DMF and dichloromethane was added and reacted for 2 days at 40° C. to obtain poly(ethylene glycol)-block-PAsp(DET) copolymer (PEG-PBLA). The degree of polymerization of the PBLA part was shown by NMR analysis to be about 68. The resulting PEG-PBLA was dissolved in benzene, freeze-dried, and dissolved in NMP in an argon atmosphere, diethylene triamine (DET) equivalent to 50 times the amount of benzyl ester was mixed with the same amount of NMP, and the PEG-PBLA solution was added to the DET solution in argon at 10° C. and reacted for 1 hour. This was added to cooled 5 N HCl aqueous solution, purified by dialysis at 4° C. with 0.01 N HCl followed by pure water, and collected by freeze-drying to obtain the target block copolymer (hereunder abbreviated as PEG-PAsp (DET).

Example 1

Preparation of Cationic Polymer-Coated Mannitol Nanoparticles, and Supporting of Anionically Charged Substance on Nanoparticle Surfaces This example confirms that nanoparticles surface-coated with PAsp(DET) can be prepared by freeze-drying a mixed solution of mannitol and the cationic polymer PAsp(DET), and that the cationic nanoparticles can support the anionic drug siRNA on their surfaces.

Figure 1:
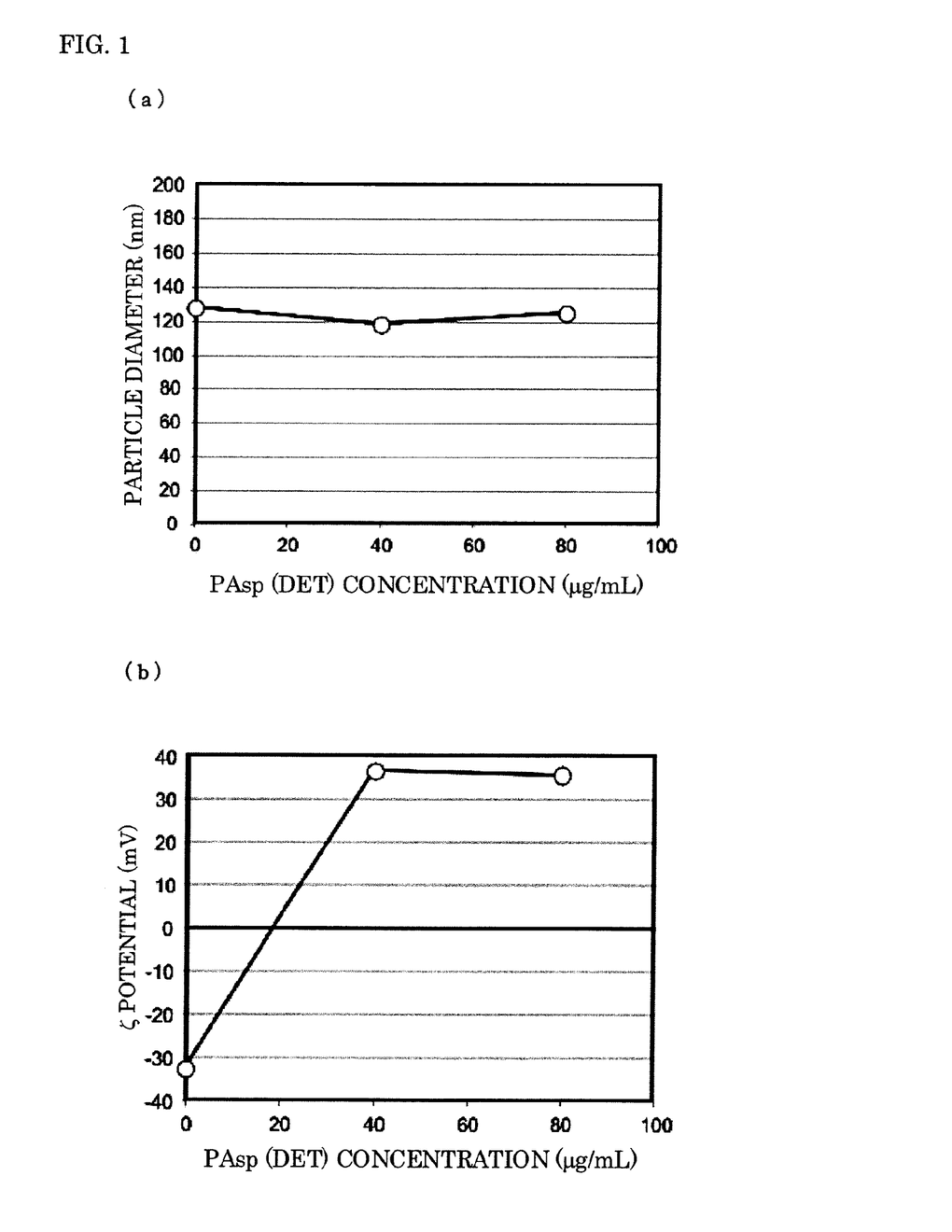
FIG. 1 is a graph of the particle diameter (a) and surface potential (b) of the mannitol/PAsp(DET) nanoparticles of Example 1(1) of the present invention.

MATERIALS AND METHODS (1) 20 w/v % mannitol stock solution and 5 mg/mL PAsp (DET) (degree of polymerization about 100) stock solution were each prepared in 10 mM Hepes buffer (pH 7.3). The solutions were mixed at various concentrations to prepare mannitol/PAsp(DET) mixed solutions. Specifically, three mixed solutions were prepared with a mannitol concentration of 5 w/v % and PAsp(DET) concentrations of 0, 40 and 80 µg/mL. These solutions were placed in sample tubes, and rapid-frozen by immersion in liquid nitrogen. These were then set in a freeze-drying unit (DRC-1000/FDU1100 (shelf type) or FDU-2100 (manifold type), EYELA), and dried for 2 to 3 days. Pure water was added to rehydrate the freeze-dried samples, and the particle diameter and surface potential were measured with a ZetaSizer (Malvern). The results are shown in FIG. 1. As shown in FIG. 1(a), the freeze-dried mannitol was confirmed to have a particle diameter of about 120 nm whether or not PAsp(DET) was present. As shown in FIG. 1(b), the surface potential of the particles was shown to be negative (about −30 mV) when no PAsp(DET) was added and positive (about +35 mV) when PAsp(DET) was added. It appears from this that cationic nanoparticles were prepared comprising mannitol cores covered with PAsp(DET).

Figure 2:
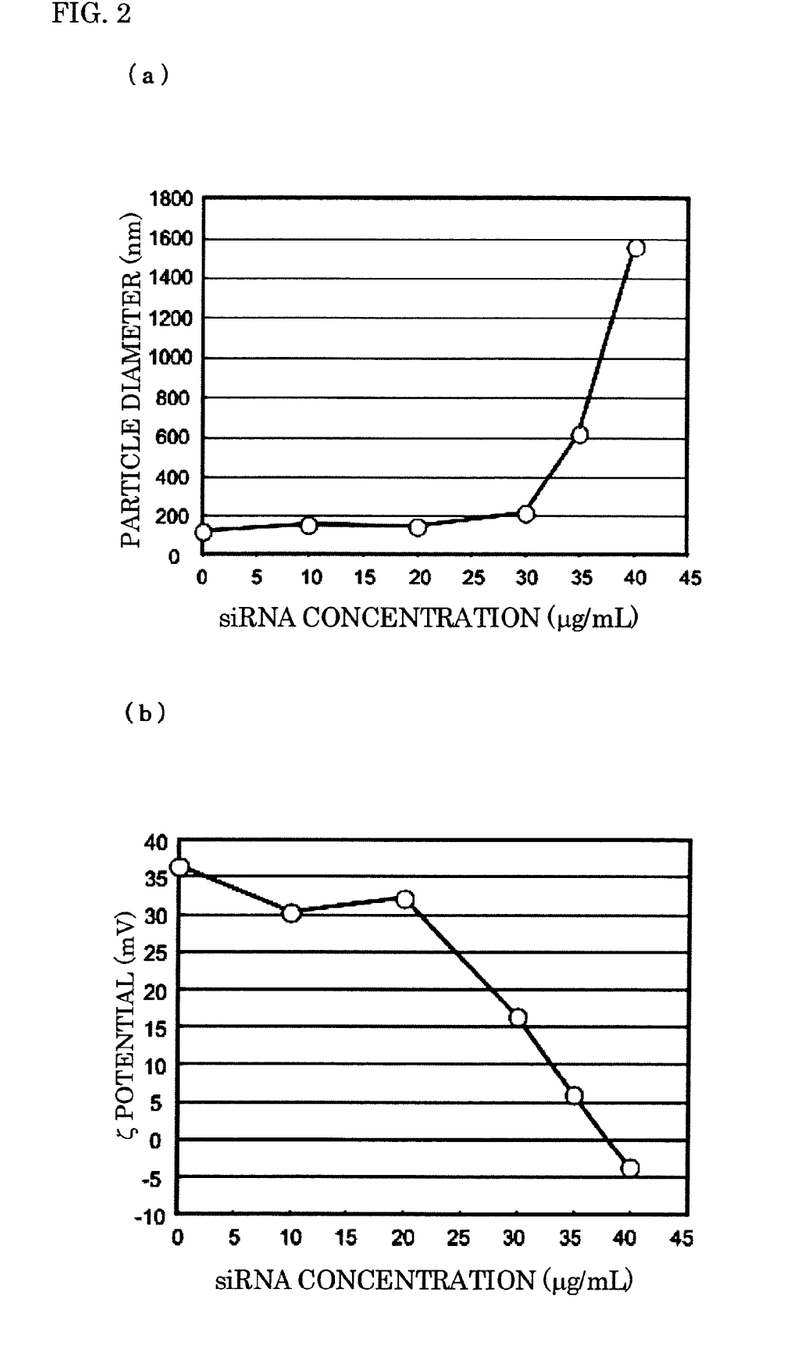
FIG. 2 is a graph of the particle diameter (a) and surface potential (b) of the mannitol/PAsp(DET)/siRNA nanoparticles of Example 1(2) of the present invention.

(2) Next, siRNA solutions of various concentrations (0, 10, 20, 30, 35 and 40 µg/mL) were added to nanoparticles prepared with a PAsp(DET) concentration of 40 µg/mL in order to confirm whether the resulting cationic nanoparticles were capable of supporting the anionic drug siRNA. These mixed solutions were then subjected again to particle diameter and surface potential measurement. The results are shown in FIG. 2. FIG. 2(a) shows results for particle diameter and FIG. 2(b) for surface potential. As shown in FIG. 2(a), the particle diameter was shown to rise slightly as the siRNA concentration increased, and large particles were confirmed at 35 µg/mL and above. As shown in FIG. 2(b), the surface potential decreased gradually as the siRNA concentration increased, suggesting adsorption of siRNA on the surfaces of the cationic nanoparticles. The surface potential of the nanoparticles was close to neutral at the siRNA concentrations (35, 40 μg/mL) at which the particle diameter was greatest, suggesting a decrease in dispersion stability.

Example 2

One-Step Nanoparticle Preparation with Mannitol, Cationic Polymer PAsp(DET) and Anionic Drug siRNA, and Introduction of siRNA into Cultured Cells In this example, preparation of nanoparticles comprising a core of mannitol coated with PAsp(DET) and siRNA was confirmed by freeze-drying a mixed solution of mannitol, the cationic polymer PAsp(DET) and siRNA, and introduction of siRNA into cultured cells was evaluated.

Figure 3:
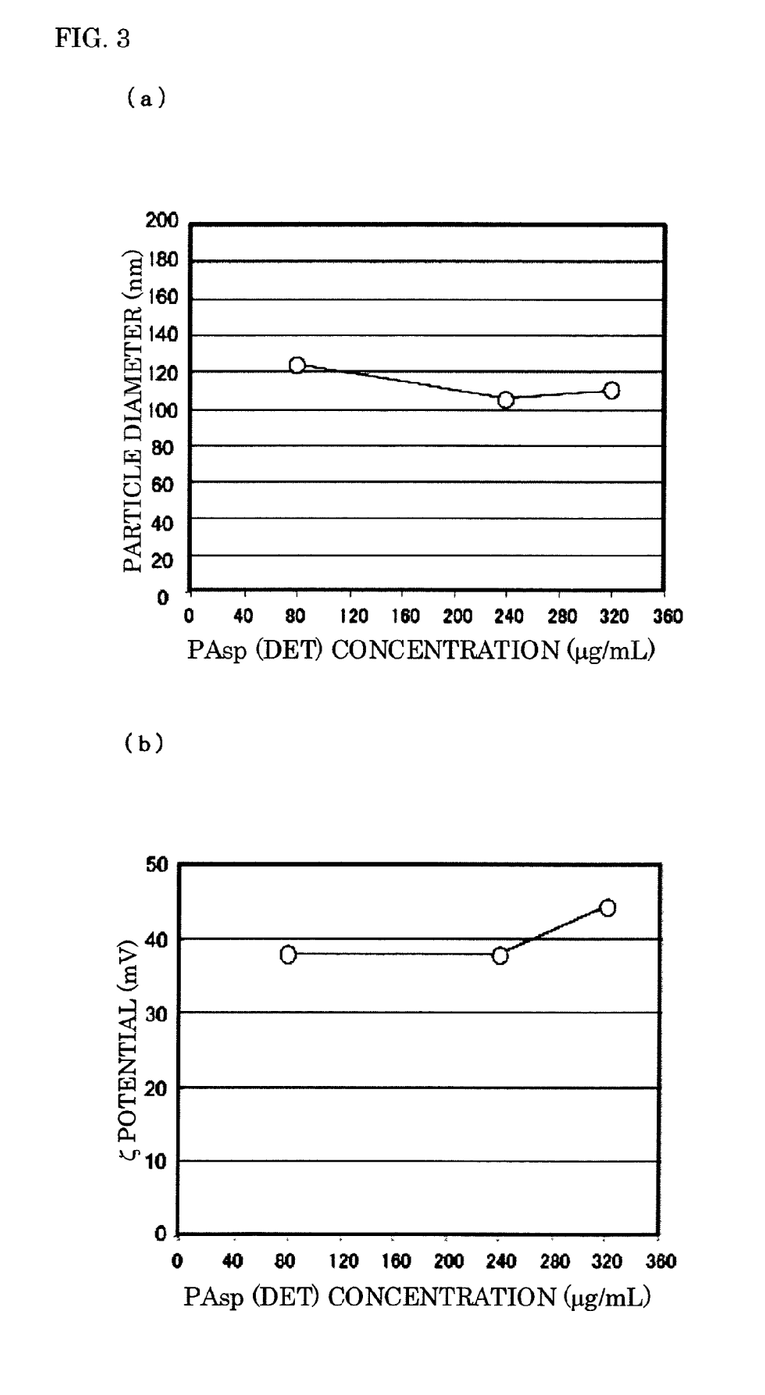
FIG. 3 is a graph of the particle diameter (a) and surface potential (b) of the mannitol/PAsp(DET)/siRNA nanoparticles of Example 2(1) of the present invention.

MATERIALS AND METHODS (1) 20 w/v % mannitol stock solution, 5 mg/mL PAsp (DET) (degree of polymerization about 100) stock solution and 15 M siRNA stock solution were each prepared in 10 mM Hepes buffer (pH 7.3). These solution were mixed at various concentrations to prepare mannitol/PAsp(DET)/siRNA mixed solutions. Specifically, three mixed solutions were prepared with a mannitol concentration of 5 w/v %, a siRNA concentration of 0.75 M and PAsp(DET) concentrations of 80, 240 and 320 μg/mL. These solutions were placed in sample tubes, and rapid-frozen by immersion in liquid nitrogen. These were then set in a freeze-drying unit (DRC-1000/FDU1100 (shelf type) or FDU-2100 (manifold type), EYELA), and dried for 2 to 3 days. Pure water was added to rehydrate the freeze-dried samples, and the particle diameter and surface potential were measured with a ZetaSizer (Malvern). The results are shown in FIG. 3. As shown in FIG. 3(a), the freeze-dried samples were confirmed to have particle diameters of about 110 nm. As shown in FIG. 3(b), the surface potential of the particles was confirmed to be about 40 mV.

Figure 4:
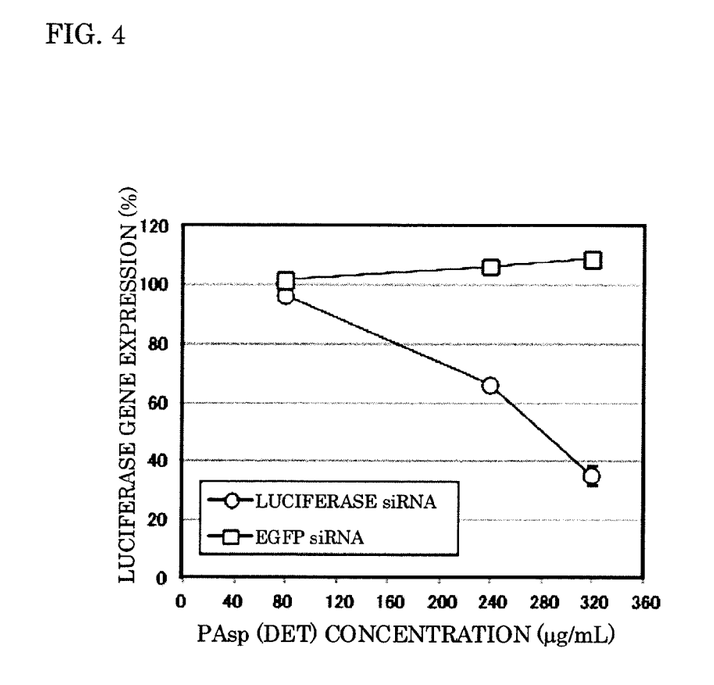
FIG. 4 is a graph of the RNAi activity of the mannitol/PAsp(DET)/siRNA nanoparticles of Example 2(2) of the present invention.

(2) Next, nanoparticles obtained with a siRNA concentration of 100 nM were incubated with cultured cells (GL3-luciferase-expressing mouse melanoma B16F10). Two different siRNA sequences were used, one that corresponded to the GL3-luciferase gene and one that did not (EGFP sequence). After 48 hours, the amount of the GL3-luciferase protein was assayed with a luciferase assay kit (Promega). The results are shown in FIG. 4. As shown in FIG. 4, the amount of GL3-luciferase was shown to decrease dose-dependently with the amount of PAsp(DET) when GL3-siRNA was used. When EGFP-siRNA was used, on the other hand, there was no decrease in GL3-luciferase, confirming both a siRNA sequence-dependent gene silencing effect and extremely low toxicity of the mannitol/PAsp(DET)/siRNA nanoparticles themselves.

Example 3

Figure 5:
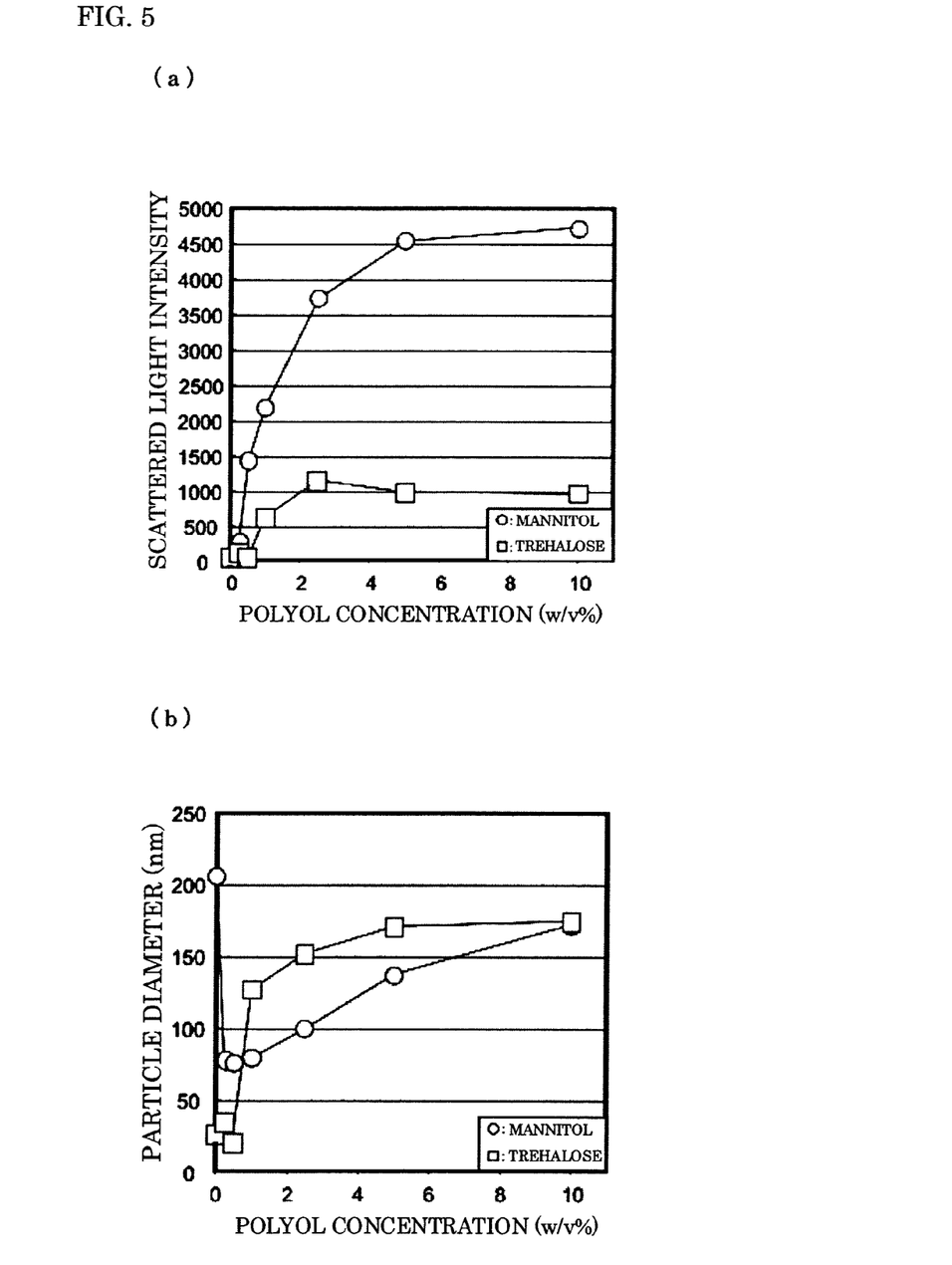
FIG. 5 is a graph of the scattered light intensity (a) and particle diameter (b) of the trehalose/PAsp(DET) nanoparticles of Example 3 of the present invention.

Fine particles were obtained by repeating the same operations as in Example 2(1) except that 0, 0.25, 0.5, 1, 2.5, 5 and 10 w/v % of trehalose was used instead of the mannitol of Example 2, with a PAsp(DET) concentration of 80 μg/mL, and the results for scattered light intensity (a) and particle diameter (b) are shown in FIG. 5 together with the results using mannitol.

The results of FIG. 5(a) show significant scattered light intensity using trehalose at concentrations of 1 w/v % or above, indicating the nanoparticles were prepared. The particle diameters of the nanoparticles were confirmed to be 120 to 180 nm as shown in FIG. 5(b). The concentration required for preparing nanoparticles was higher than with mannitol, and the association number of the nanoparticles was lower (the association number (molecular weight) of nanoparticles is increased with the increase in the scattered light intensity).

Example 4

Figure 6:
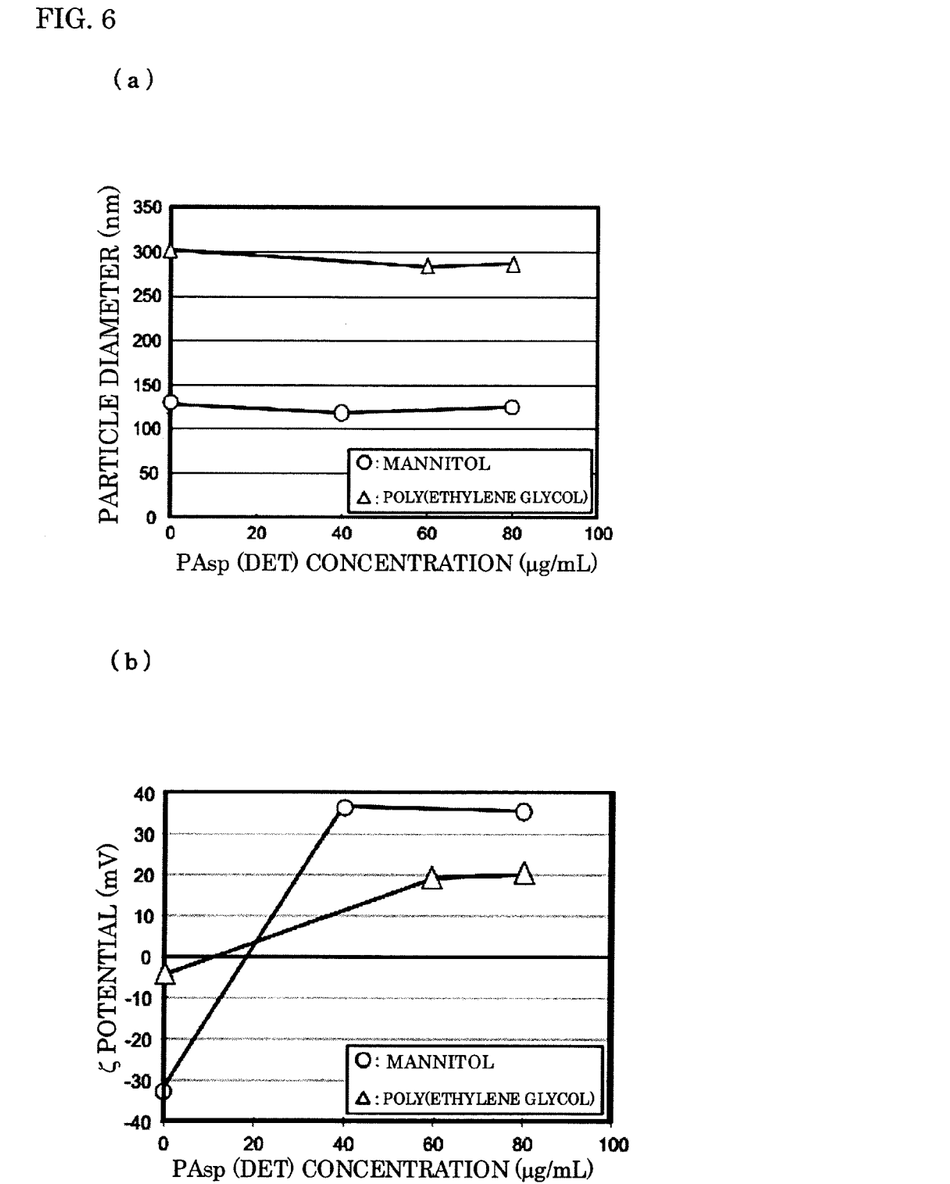
FIG. 6 is a graph of the particle diameter (a) and surface potential (b) of the PEG/PAsp(DET) nanoparticles of Example 4 of the present invention.

Fine particles were obtained by repeating the same operations as in Example 2(1) but using, in place of the mannitol in Example 2, poly(ethylene glycol) (molecular weight 6000) and PAsp(DET) concentrations of 60 and 80 μg/mL, and the results for particle diameter (a) and surface potential (b) are shown in FIG. 6 together with the results using mannitol.

FIG. 6(a) shows that 300 nm nanoparticles were prepared using poly(ethylene glycol). The ζ potential of the prepared nanoparticles was about −5 mV, or slightly negative without PAsp(DET), but rose to about +20 mV when PAsp(DET) was added, confirming that PAsp(DET) was supported on the nanoparticle surfaces. The particle diameter was larger than with mannitol, and the ζ potential was lower.

Example 5

Figure 7:
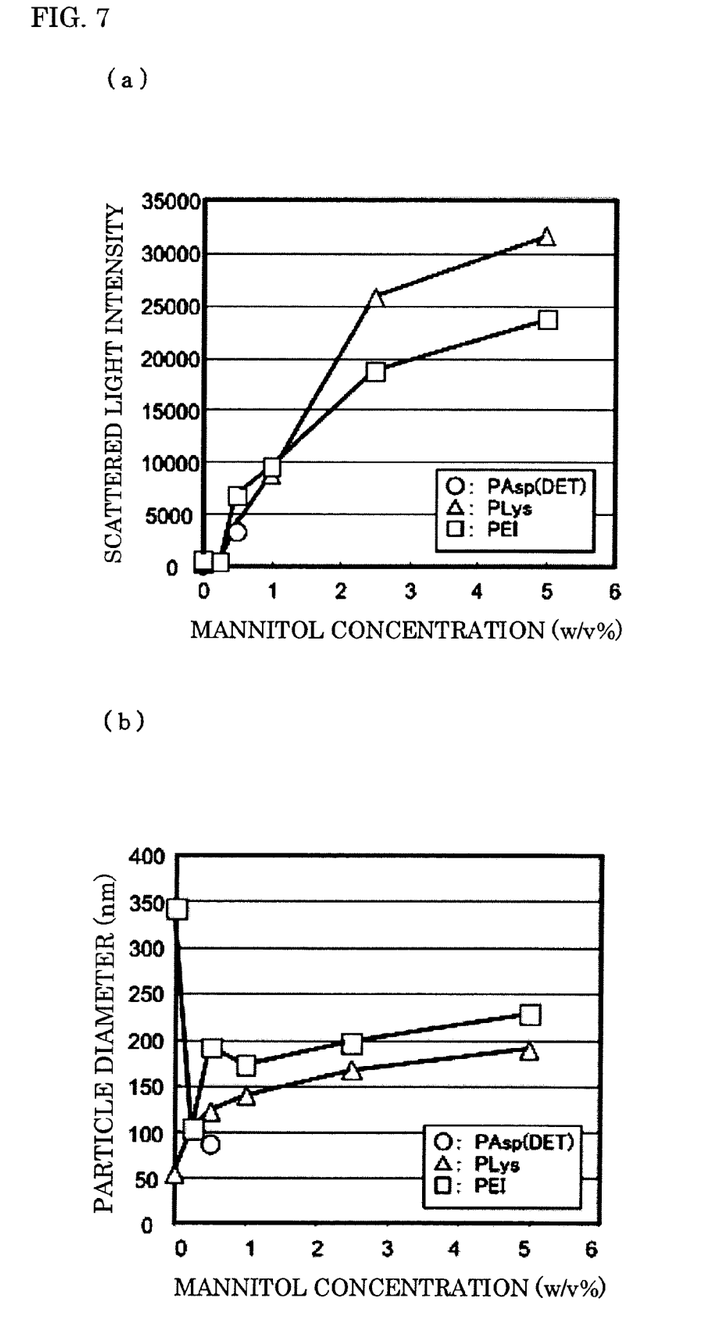
FIG. 7 is a graph of the scattered light intensity (a) and particle diameter (b) of the mannitol/PLys or mannitol/PEI nanoparticles of Example 5 of the present invention.

Fine particles were obtained by repeating the same operations as in Example 2 except that 50 μg/mL of polyethyleneimine (molecular weight 5000, PEI) or 130 μg/mL of polylysine (molecular weight 18000, PLys) was used instead of PAsp(DET) in Example 2, and the results for scattered light intensity (a) and particle diameter (b) are shown in FIG. 7 together with the results using 80 μg/mL of PAsp(DET).

FIG. 7(a) shows significant scattered light intensity at mannitol concentrations of 0.5 w/v % and above, indicating that nanoparticles were prepared using PEI or PLys as they were using PAsp(DET). FIG. 7(b) confirms that the particle diameters of the prepared nanoparticles were 120 to 230 nm.

Example 6

Figure 8:
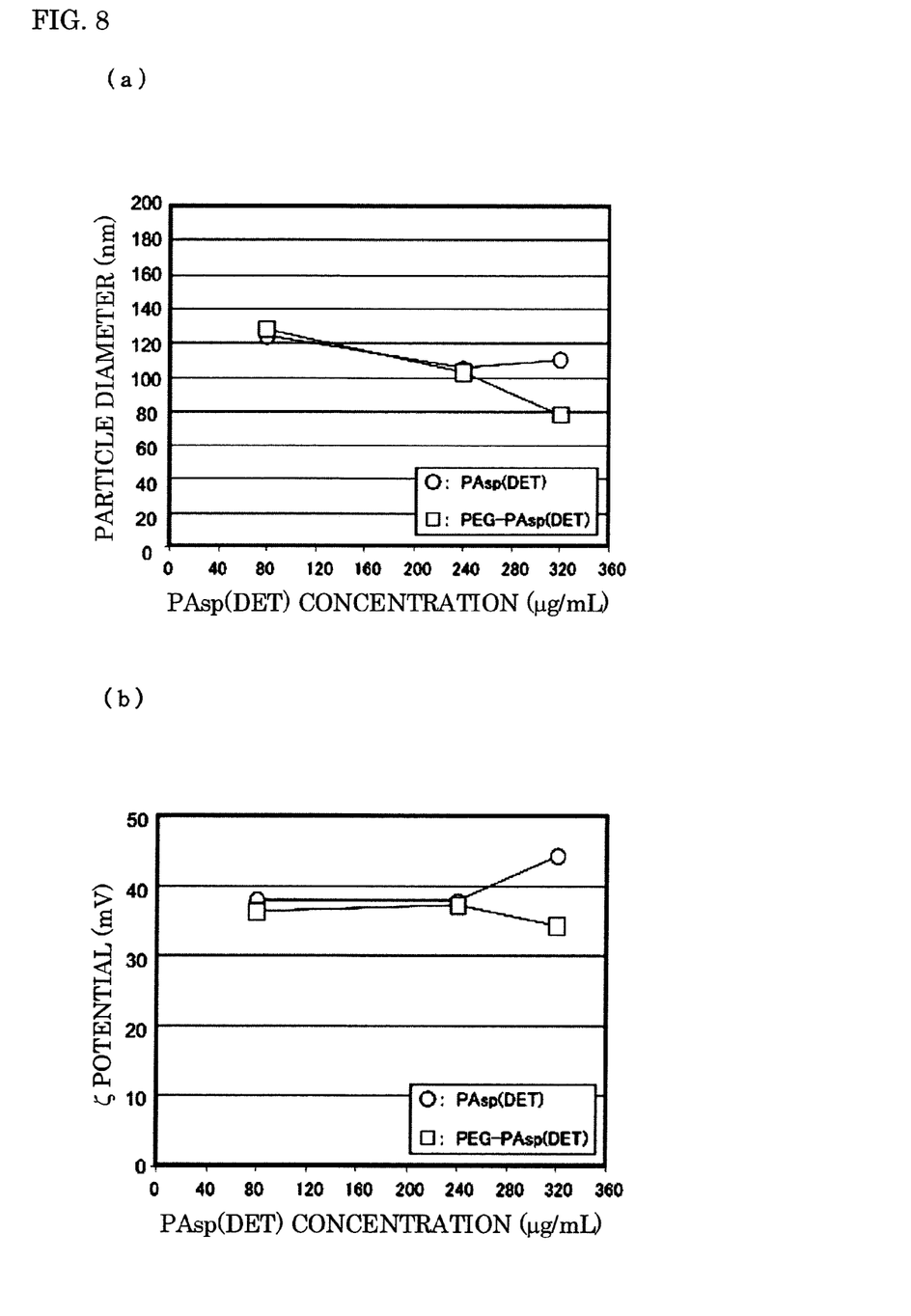
FIG. 8 is a graph of the particle diameter (a) and surface potential (b) of the mannitol/PEG-PAsp(DET) nanoparticles of Example 6 of the present invention.

Fine particles were obtained by repeating the same operations as in Example 2 except that PEG-PAsp(DET) was used instead of the PAsp(DET) of Example 2, and the results for particle diameter (a) and surface potential (b) are shown in FIG. 8 together with the results using PAsp(DET).

FIG. 8(a) shows that as in the case of PAsp(DET), nanoparticles with a particle diameter of 80 to 130 nm were prepared using PEG-PAsp(DET). The ζ potential was also similar at +30 to 40 mV.

INDUSTRIAL APPLICABILITY

The present invention is applicable to pharmaceutical manufacture for example because it provides a pharmaceutical drug carrier capable of stably and effectively carrying an anionically charged drug on its surface, together with a conjugate of these with a biologically active substance.

The invention claimed is:

1. A method of preparing fine particles of crystalline polyol having a cationic polymer fixed on the surface thereof, the method comprising freeze-drying an aqueous solution containing both a crystalline polyol and a cationic polymer and obtaining fine particles of crystalline polyol having a cationic polymer fixed on the surface thereof,
wherein the cationic polymer is selected from the group consisting of polylysine; polyarginine; spermine; spermidine; polyethyleneimine; poly(polyamine-modified aspartamide); poly(polyamine-modified glutamide); and copolymers comprising blocks of polymer chains derived from polylysine, polyarginine, spermine, spermidine, polyethyleneimine, poly(polyamine-modified aspartamide), or poly(polyamine-modified glutamide); and blocks of polymer chains derived from poly(ethylene glycol), and the aqueous solution containing both a crystalline polyol and a cationic polymer is a mixture of a crystalline polyol aqueous solution with a concentration of 0.1 to 10 w/v % and a cationic polymer aqueous solution with a concentration of 1 to 1000 μg/mL.

2. The method according to claim 1, wherein the crystalline polyol is in a crystalline state in the fine particles of crystalline polyol.

3. The method according to claim 1, wherein the crystalline polyol is selected from the group consisting of mannitol, trehalose, xylitol, sorbitol, inositol, glucose, galactose, sucrose, mannose, fructose, ribose, xylose, dextrin and poly(ethylene glycol) having 10 to 2500 oxyethylene units.

4. The method according to claim 1, wherein the obtained fine particles have an average particle diameter of 10 to 1000 nm and a positive ζ potential on surfaces thereof when measured in pure water.

5. The method according to claim 4, wherein the surface ζ potential is +5 to +100 mV.

6. The method according to claim 1, wherein the cationic polymer is represented by Formula (1) below:

(1)

wherein:
R$^1$ represents a hydroxyl group, C$_{1\text{-}12}$ optionally substituted straight or branched alkyloxy group, C$_{2\text{-}12}$ optionally substituted straight or branched alkenyloxy group, C$_{1\text{-}12}$ optionally substituted straight or branched alkynyloxy group or C$_{1\text{-}12}$ optionally substituted straight or branched alkyl-substituted imino group;

R$^2$ represents a hydrogen atom, C$_{1\text{-}12}$ optionally substituted straight or branched alkyl group or C$_{1\text{-}24}$ optionally substituted straight or branched alkylcarbonyl group;

R$^{3a}$ and R$^{3b}$ each independently represent a methylene group or ethylene group; and R$^{4a}$ and R$^{4b}$ independently represent the same or different groups selected from the group consisting of:

(i),

(ii), (iii), and (iv)

wherein p1 to p4, q1 to q6 and r1 and r2 are all independently integers from 1 to 20, n is an integer from 0 to 5,000, and y is an integer from 0 to 5,000, but when R$^{3a}$ and R$^{3b}$ are methylene groups, n is 5 or greater, and y is an integer smaller than n.

7. The method according to claim 6, wherein the cationic polymer is the block copolymer represented by Formula (2) below:

(2)

wherein R$^2$, R$^{3a}$, R$^{3b}$, R$^{4a}$, R$^{4b}$, n and y are as defined in Formula (1); L$^1$ is —S—S— or a valence bond; L$^2$ is —NH—, —O—, —O(CH$_2$)$_{p1}$—NH— or -L$^{2a}$-(CH$_2$)$_{q1}$-L$^{2b}$, with p1 and q1 each being independently an integer from 1 to 20; L$^{2a}$ is OCO, OCONH, NHCO, NHCO, NHCOO, NHCONH, CONH or COO and L$^{2b}$ is NH or O; R$^5$ is a hydrogen atom or an optionally substituted C$_{1\text{-}12}$ straight or branched alkyl group; and m is an integer from 30 to 20,000.

* * * * *